(12) United States Patent
Hori (10) Patent No.: US 11,491,307 B2
(45) Date of Patent: Nov. 8, 2022

(54) CATHETER

(71) Applicant: ASAHI INTECC CO., LTD., Seto (JP)

(72) Inventor: Takayuki Hori, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 562 days.

(21) Appl. No.: 16/553,255

(22) Filed: Aug. 28, 2019

(65) Prior Publication Data

US 2019/0381278 A1 Dec. 19, 2019

Related U.S. Application Data

(63) Continuation of application No. PCT/JP2017/009693, filed on Mar. 10, 2017.

(51) Int. Cl.
*A61M 25/00* (2006.01)

(52) U.S. Cl.
CPC .... *A61M 25/0053* (2013.01); *A61M 25/0045* (2013.01); *A61M 25/0067* (2013.01); *A61M 2025/0059* (2013.01)

(58) Field of Classification Search
CPC .......... A61M 25/0053; A61M 25/0045; A61M 25/00657; A61M 25/0005; A61M 2025/0059
See application file for complete search history.

(56) References Cited

U.S. PATENT DOCUMENTS

| 6,030,371 | A | * | 2/2000 | Pursley | A61M 25/0009 |
| | | | | | 427/2.12 |
| 2002/0022825 | A1 | | 2/2002 | Saitou et al. | |
| 2005/0131387 | A1 | * | 6/2005 | Pursley | A61M 25/005 |
| | | | | | 604/524 |
| 2006/0030835 | A1 | * | 2/2006 | Sherman | A61F 2/958 |
| | | | | | 604/526 |
| 2015/0335857 | A1 | * | 11/2015 | Ishikawa | A61M 25/005 |
| | | | | | 604/526 |

FOREIGN PATENT DOCUMENTS

| CN | 101001658 A | 7/2007 |
| EP | 1123714 A1 | 8/2001 |
| EP | 1787674 A1 | 5/2007 |
| JP | H08-71157 A | 3/1996 |
| JP | 2001-218851 A | 8/2001 |
| JP | 2006-223728 A | 8/2006 |
| JP | 2007-000392 A | 1/2007 |
| JP | 3915862 B2 | 5/2007 |
| JP | 5927974 B2 | 6/2016 |
| WO | 2006/016481 A1 | 2/2006 |

OTHER PUBLICATIONS

Jun. 13, 2017 International Search Report issued in International Patent Application No. PCT/JP2017/009693.

* cited by examiner

*Primary Examiner* — Laura A Bouchelle
*Assistant Examiner* — John A Doubrava
(74) *Attorney, Agent, or Firm* — Oliff PLC (57) ABSTRACT

A catheter having a proximal end portion having gaps between axially adjacent portions of an element wire where an inner layer is joined to an outer layer through the gaps; and a distal end portion where the axially adjacent portions of the element wire come into contact with each other, and a cavity is provided between the inner layer and a coil body. The catheter has excellent followability to a guide wire and is capable of efficiently transmitting a pushing force and/or rotational force from an operator to the distal end of the catheter.

14 Claims, 12 Drawing Sheets

CATHETER

CROSS REFERENCE TO RELATED APPLICATION

This is a Continuation of PCT/JP2017/009693 filed Mar. 10, 2017. The disclosure of the prior application is hereby incorporated by reference herein in its entirety.

BACKGROUND

The disclosed embodiments relate to a medical device, and specifically relate to a catheter.

A narrowed or obstructed segment formed in a blood vessel, bile duct, pancreatic duct, and the like can inhibit the flow of blood, gall (bile), pancreatic juice, and the like, respectively. Catheter treatment is widely used as a method of treating such a narrowed or obstructed segment.

A blood vessel, bile duct, pancreatic duct, and the like each have an inner cavity (lumen) which is thinner and more significantly curved toward the end thereof. Accordingly, if a narrowed or obstructed segment is formed at the end of a blood vessel, bile duct, pancreatic duct, or the like, a pre-inserted guide wire may be strongly curved along with the blood vessel, bile duct, pancreatic duct, or the like. For this reason, a catheter needs to be able to follow a curved guide wire (that is, have "followability"). Further, a catheter needs to be able to efficiently transmit a pushing force and/or rotational force from an operator to the distal end of the catheter (that is, have "pushability") so that the catheter can be pushed to a narrowed or obstructed segment to be treated.

In general, a catheter includes an inner layer, a coil body configured such that an element wire(s) is/are wound around on an outer periphery of the inner layer, and an outer layer covering an outer layer of the coil body (see Japanese Patent Nos. 3915862 and 5927974, described below).

However, the coil body in the catheter described in Japanese Patent No. 3915862 is entirely covered and fixed with the inner layer and the outer layer throughout the length thereof. This configuration, disadvantageously, may restrict movement of the element wire of the coil body along the curvature of a curved catheter (in other words, the degree of freedom of the element wire is poor), resulting in poor followability to a guide wire.

Further, a catheter described in Japanese Patent No. 5927974 includes a cavity between an inner layer and a coil body and/or between the coil body and an outer layer. Disadvantageously, axially adjacent element wires in this configuration do not come into contact with each other, resulting in inefficient transmission of a pushing force and/or rotational force from an operator to the distal end of the catheter.

SUMMARY

The disclosed embodiments were devised in view of the above circumstances. An object of the disclosed embodiments is to provide a catheter having excellent followability to a guide wire and that is capable of efficiently transmitting a pushing force and/or rotational force from an operator to the distal end of the catheter.

The above object can be achieved by the means as listed below.

A catheter of the disclosed embodiments includes an inner layer; a coil body including one or more element wires wound around an outer periphery of the inner layer; and an outer layer covering an outer periphery of the coil body. The catheter has a proximal end portion having gaps between axially adjacent portions of the element wires, and where the inner layer is joined to the outer layer through the gaps between the axially adjacent portions of the element wires; and a distal end portion where the axially adjacent portions of the element wires come into contact with each other, and a cavity is formed between the inner layer and the coil body, the distal end portion being located at a distal end side relative to the proximal end portion.

In this configuration, the element wires of the coil body, which is not completely fixed to the inner layer and the outer layer, and thus has some degree of freedom, can be flexible enough to be curved at the distal end portion of the catheter when the catheter is curved. This can improve followability to a pre-inserted curved guide wire. Further, the element wires of the coil body axially coming into contact with each other with some degree of freedom can allow a rotational force to be transmitted from an operator to the distal end of the catheter. Moreover, the element wires fixed between the inner layer and the outer layer at the proximal end portion can improve the stiffness of the catheter shaft, leading to efficient transmission of a pushing force from an operator.

The catheter may include an intermediate portion provided between the proximal end portion and the distal end portion, and in which the gaps between the axially adjacent portions of the element wires become wider toward a proximal end. The cavity at the distal end portion extends to the intermediate portion, and the height of the cavity gradually decreases toward the proximal end of the intermediate portion.

This configuration can reduce a sudden change in stiffness between the proximal end portion and the distal end portion, and thus can prevent a kink and/or break between the proximal end portion and the distal end portion.

DETAILED DESCRIPTION OF EMBODIMENTS

Figure 1:
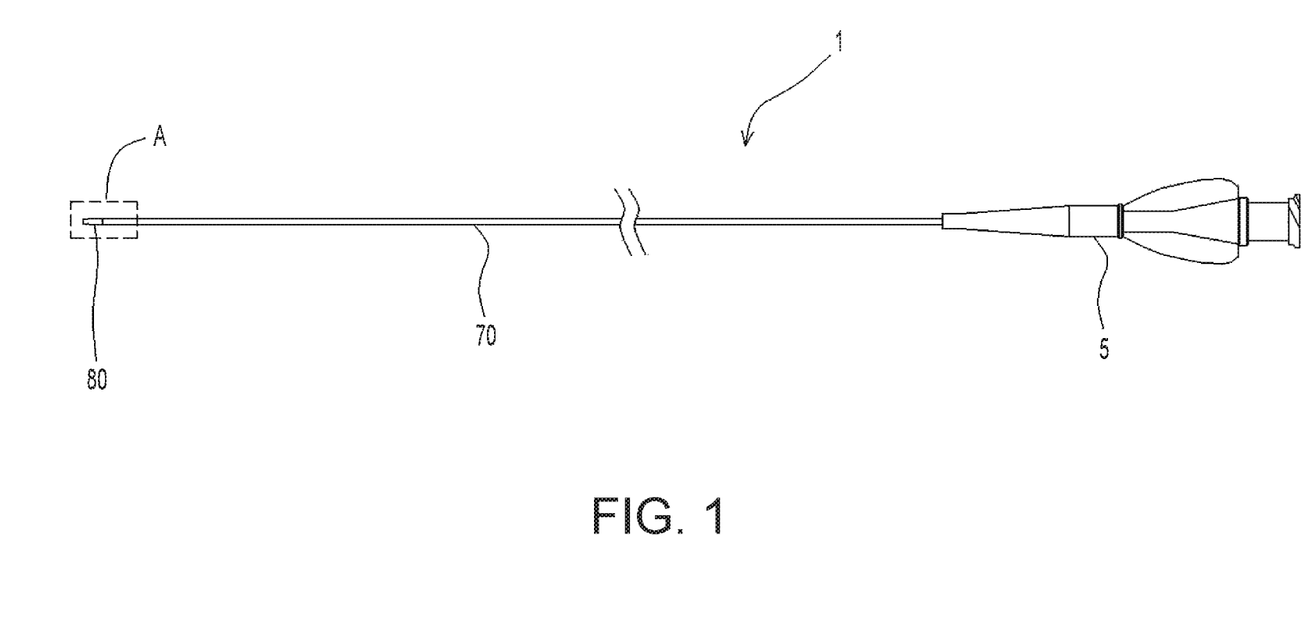
FIG. 1 is an overall view of a catheter according to the disclosed embodiments.
Figure 2:
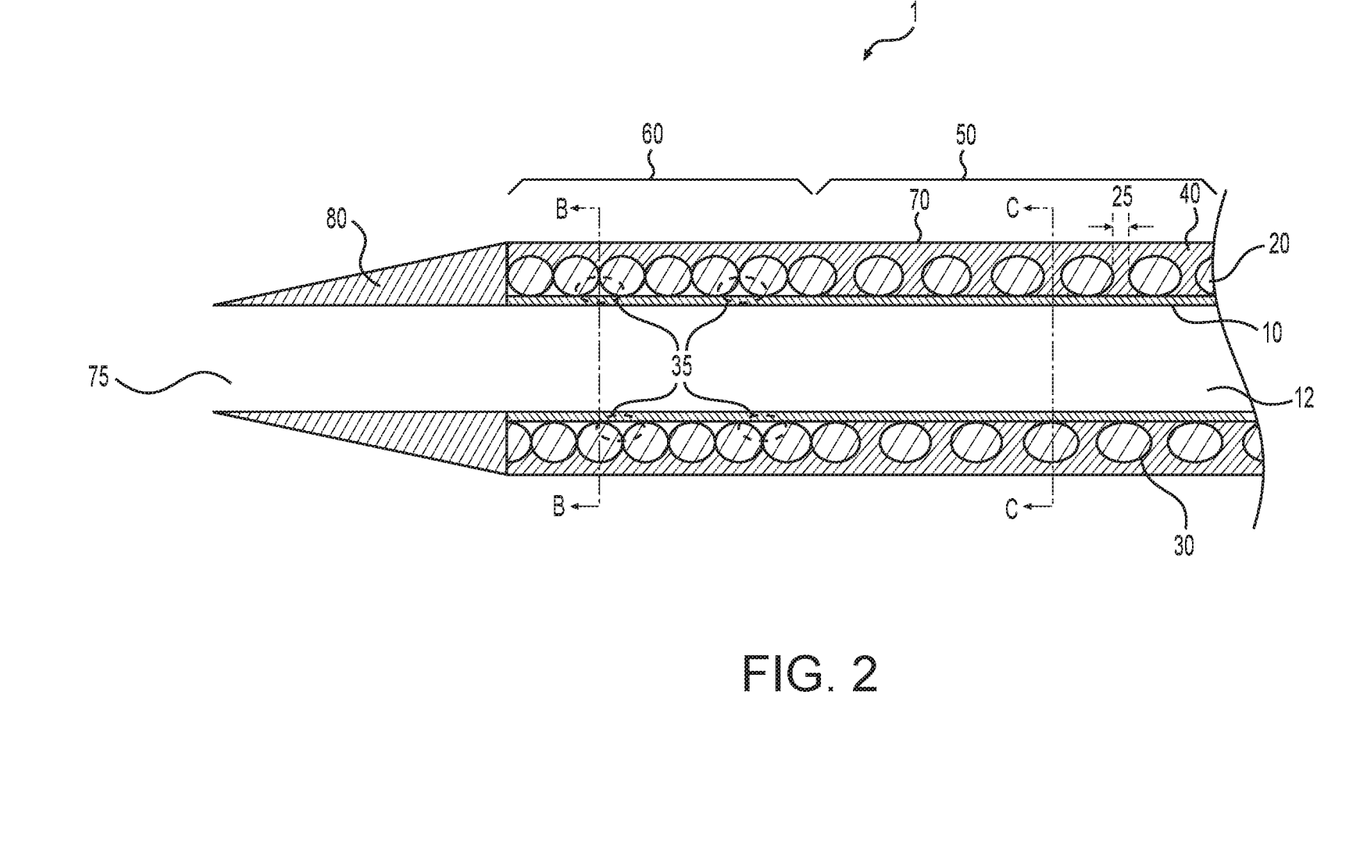
FIG. 2 is an enlarged cross-sectional view of a portion A in FIG. 1.

A catheter 1 according to the disclosed embodiments will be described with reference to FIGS. 1 to 4. In FIGS. 1 and 2, the left side in the figures corresponds to the distal end side (the distal side) which is to be inserted into the body, and the right side corresponds to the proximal end side (the proximal side) which is to be operated by an operator such as a physician. FIG. 2 is an enlarged cross-sectional view of a portion A in FIG. 1.

The catheter 1 may be used, for example, to treat a narrowed or obstructed segment of a vessel. As shown in FIG. 1, the catheter 1 generally includes a catheter shaft 70, a tip 80 joined to a distal end of the catheter shaft 70, and a connector 5 joined to a proximal end of the catheter shaft 70.

As shown in FIG. 2, the catheter shaft 70 has, radially in order from the inner side, an inner layer 10, a coil body 30 including an element wire 20 that is wound around an outer periphery of the inner layer 10, and an outer layer 40 covering an outer periphery of the coil body 30.

The inner layer 10 is formed with a resin, and is a tubular structure comprising a lumen 12 through which a guide wire and other catheters can be inserted. There is no particular limitation for a resin material with which the inner layer 10 is formed. For example, polytetrafluoroethylene (PTFE) can be used.

The coil body 30 shown in FIG. 2 is formed of a single element wire 20 that is wound spirally in the clockwise direction facing to the distal end side. Stainless steel (SUS304) can be used as a material for the element wire 20 of the coil body 30, but the material is not limited to this. For example, not only metal materials such as tungsten and Ni—Ti alloys but also resin materials such reinforced plastics (e.g., polyether ether ketone (PEEK)) may be used.

The outer layer 40 is made of a resin and is formed on the outer periphery of the coil body 30. There is no particular limitation for a resin material used for forming the outer layer 40, but polyamide, polyamide elastomer, polyester, polyurethane, and the like may be used.

The tip 80 is made of a resin and is joined to the distal end of the catheter shaft 70. The tip 80 is a member with a hollow tapered shape having a tip opening 75 which is in communication with the lumen 12. There is no particular limitation for a resin used for forming the tip 80, but polyurethane, polyurethane elastomer, and the like may be used. The tip 80 may also contain a radiopaque powder. For example, when the tip 80 contains a radiopaque powder (for example, a tungsten powder) in a range between about 65 wt % and about 90 wt %, an operator such as a physician can accurately determine the position of the catheter 1 during coronary angiography.

Figure 3:
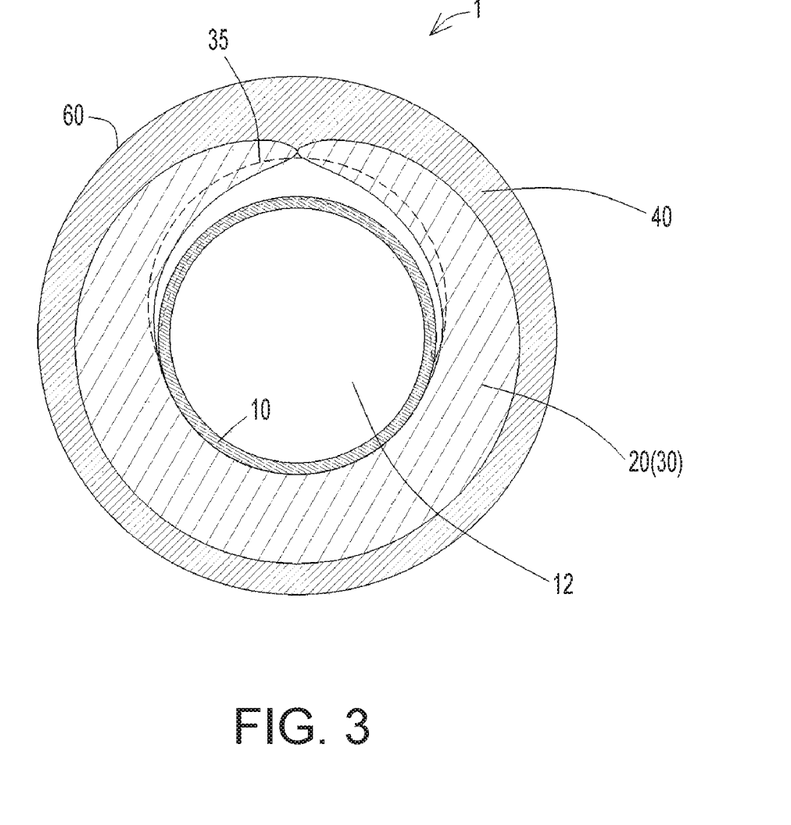
FIG. 3 is a cross-sectional view taken along line B-B of the catheter shown in FIG. 2.
Figure 4:
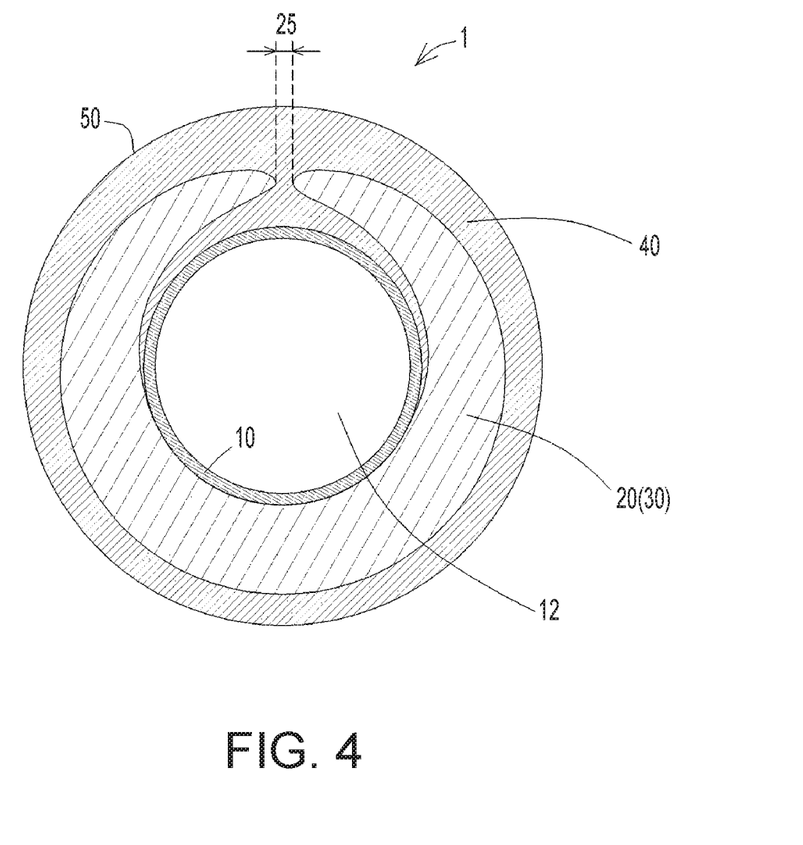
FIG. 4 is a cross-sectional view taken along line C-C of the catheter shown in FIG. 2.

The above catheter shaft 70 has a proximal end portion 50 having gaps 25 between axially adjacent portions of the element wire 20 where the inner layer 10 contacts and is directly joined to the outer layer 40 through the gaps 25 between the axially adjacent portions of the element wire 20; and a distal end portion 60 where the axially adjacent portions of the element wire 20 come into direct contact with each other, and a cavity 35 is provided between the inner layer 10 and the coil body 30, the distal end portion 60 being located at the distal end side relative to the proximal end portion 50 (see FIG. 2 to FIG. 4).

Specifically as shown in FIGS. 2 and 3, the cavity 35 as a single cavity having a substantially crescent shape in cross section is provided at the distal end portion 60 of the catheter shaft 70. The above cavity 35 is spirally formed on the outer periphery of the inner layer 10 in the axial direction of the catheter 1 along the element wire 20 of the coil body 30. Further, the adjacent portions of the element wire 20 of the coil body 30 come into contact with each other at the distal end portion 60 of the catheter shaft 70.

Meanwhile, the outer layer 40 is joined to the inner layer 10 through the gaps 25 between the adjacent portions of the element wire 20 at the proximal end portion 50 of the catheter shaft 70 as shown in FIGS. 2 and 4. This means that the element wire 20 of the coil body 30 is covered with and fixed to the inner layer 10 and the outer layer 40 along an entire circumference of the element wire 20 (and the inner layer 10 and the outer layer 40 are directly fixed to each other between the gaps 25) at the proximal end portion 50 of the catheter shaft 70.

As described above, the catheter 1 is structured differently between the distal end portion 60 and the proximal end portion 50. In this configuration, a portion of the circumference of the element wire 20 of the coil body 30 is not fixed to either the inner layer 10 or the outer layer 40, and thus the element wire 20 has some degree of freedom and can be flexible enough to be curved at the distal end portion 60 when the catheter 1 is curved. That is, the element wire 20 is movable with respect to the inner layer 10. This can improve followability to a pre-inserted curved guide wire. Further, the adjacent portions of the element wire 20 of the coil body 30 axially coming into contact with each other and having a degree of freedom can allow rotational force applied by an operator to be transmitted to the distal end of the catheter 1. Moreover, the element wires 20 of the coil body 30 fixed between the inner layer 10 and the outer layer 40 at the proximal end portion 50 can also improve the stiffness of the catheter shaft 70, leading to efficient transmission of a pushing force from an operator.

Next, a catheter 2 according to the disclosed embodiments will be described with reference to FIGS. 5 to 8. Only differences from the catheter 1 shown in FIGS. 1 to 4 will be described. The catheter 2 includes a coil body 30a formed of 10 element wires 20a that are wound spirally in the clockwise direction facing to the distal end side in place of the coil body 30 formed of the single element wire 20 (see FIGS. 6 to 8).

Figure 5:
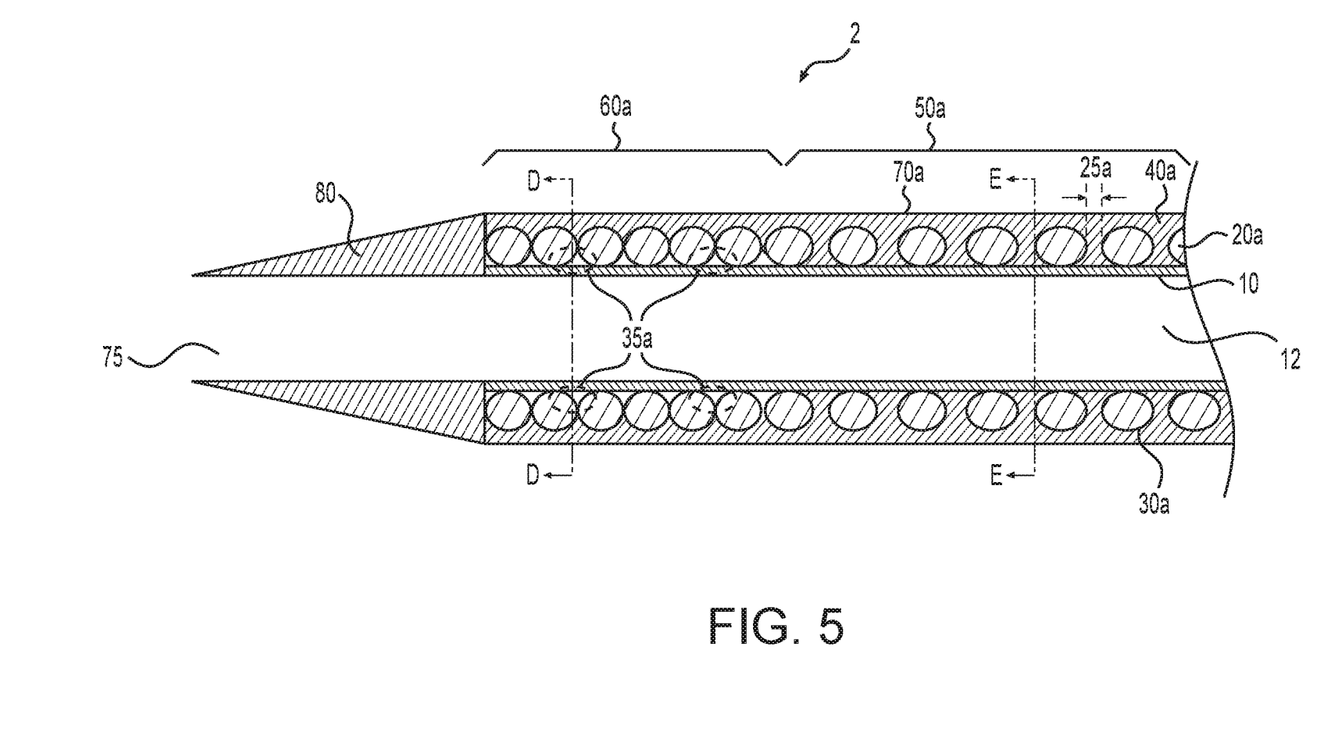
FIG. 5 is a cross-sectional view of a part of a catheter according to the disclosed embodiments.

As a material used for the element wires 20a of the coil body 30a, not only stainless steel (SUS304) but also metal materials such as tungsten and Ni—Ti alloys and resin materials such as reinforced plastics (e.g., PEEK) may be used as in the element wire 20 of the coil body 30. It is noted that the number of the element wires 20a of the coil body 30a is not limited to 10 as long as it is a plural number.

The catheter 2 includes a catheter shaft 70a including a proximal end portion 50a having gaps 25a between axially adjacent portions of the element wires 20a where the inner layer 10 is joined to an outer layer 40a through the gaps 25a between the adjacent portions of the element wires 20a; and a distal end portion 60a where the axially adjacent portions of the element wires 20a come into direct contact with each other, and cavities 35a are provided between the inner layer 10 and the coil body 30a, the distal end portion 60a being located at the distal end side relative to the proximal end portion 50a (see FIGS. 5 to 8).

Figure 6:
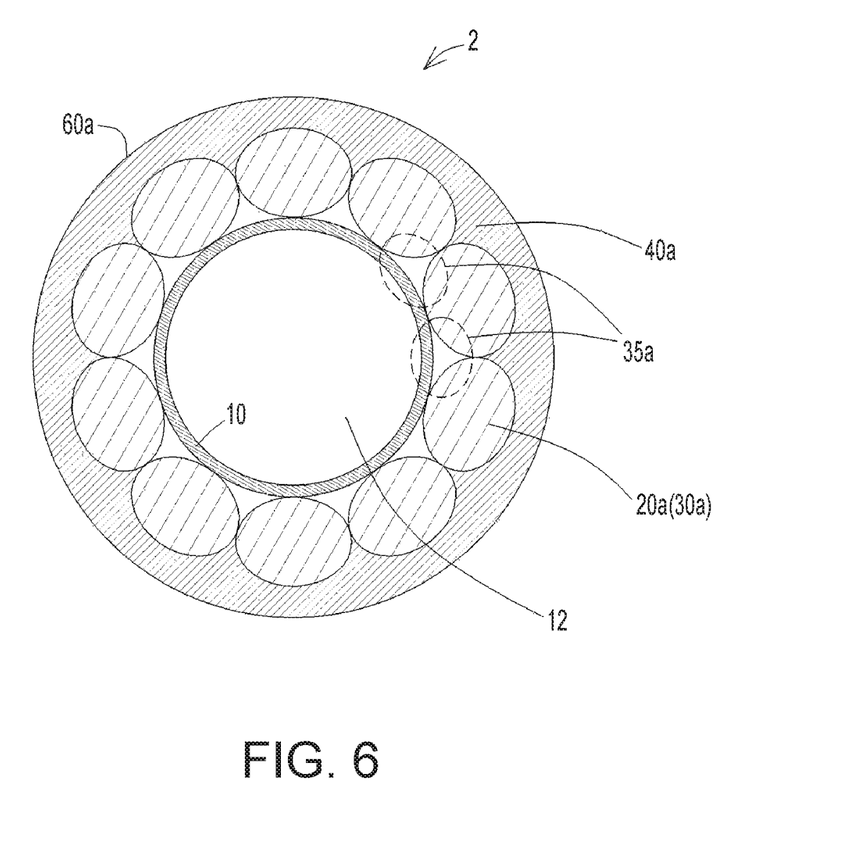
FIG. 6 is a cross-sectional view taken along line D-D of the catheter shown in FIG. 5.

Specifically as shown in FIGS. 5 and 6, 10 cavities 35a each having a substantially triangular shape in cross section are defined by circumferentially adjacent portions of the element wires 20a and the inner layer 10 at the distal end portion 60a of the catheter shaft 70a. Each of the above cavities 35a is formed spirally and axially on the outer periphery of the inner layer 10 along the 10 element wires 20a of the coil body 30a (see FIG. 8). Further, the adjacent portions of the element wires 20a of the coil body 30a come into contact with each other at the distal end portion 60a of the catheter shaft 70a.

Figure 7:
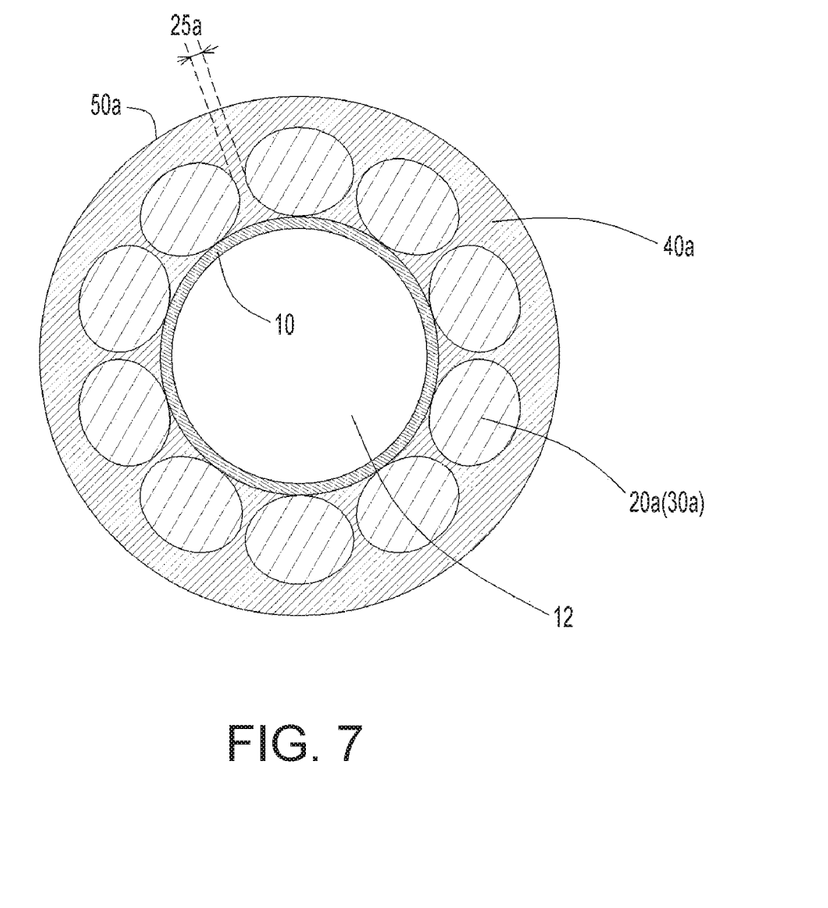
FIG. 7 is a cross-sectional view taken along line E-E of the catheter shown in FIG. 5.
Figure 8:
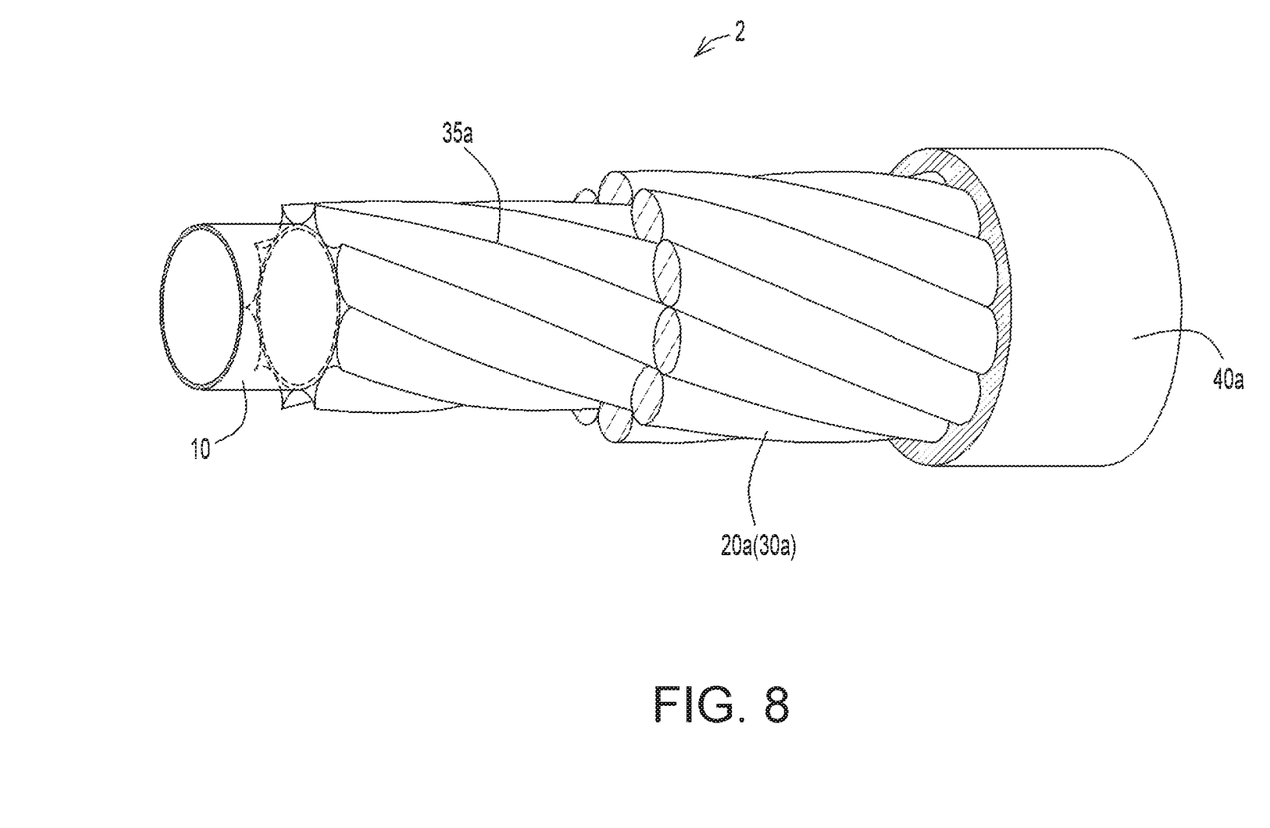
FIG. 8 shows the external appearance of a part of the catheter shown in FIG. 5. It is noted that a cutaway view is shown for better understanding where a part of an outer layer, a part of a coil body, and a part of cavities are removed.

Meanwhile, the outer layer 40a is joined to the inner layer 10 through the gaps 25a between the adjacent portions of the element wires 20a at the proximal end portion 50a of the catheter shaft 70a as shown in FIGS. 5 and 7. This means that the element wires 20a of the coil body 30a are covered with and fixed to the inner layer 10 and the outer layer 40a along an entire circumference of each of the element wires 20a (and the inner layer 10 and the outer layer 40a are directly fixed to each other between the gaps 25a) at the proximal end portion 50a of the catheter shaft 70a.

As described above, the catheter 2 is structured differently between the distal end portion 60a and the proximal end portion 50a. In this configuration, a portion of the circumference of each of the element wires 20a of the coil body 30a is not fixed to either the inner layer 10 or the outer layer 40a, and thus the element wires 20a have some degree of freedom and can be flexible enough to be curved at the distal end portion 60a when the catheter 2 is curved. This can improve followability to a pre-inserted curved guide. Further, the adjacent portions of the element wires 20a of the coil body 30a axially coming into contact with each other and having a degree of freedom can allow a rotational force from an operator to be transmitted to the distal end of the catheter 2. Moreover, the element wires 20a of the coil body 30a fixed between the inner layer 10 and the outer layer 40a at the proximal end portion 50a can improve the stiffness of the catheter shaft 70a, leading to efficient transmission of a pushing force from an operator.

Further, in the catheter 2, the cavities 35a of the distal end portion 60a provide increased spacing between the inner layer 10 and the coil body 30a as compared with the single cavity 35 of the distal end portion 60 of the catheter 1. This, in turn, can further increase the degree of freedom for the element wires 20a of the coil body 30a at the distal end portion 60a, leading to further improved followability to a guide wire. Further, the element wires 20a of the coil body 30a can axially come into contact with each other more reliably when the catheter 2 is rotated by an operator as compared with the element wire 20 of the coil body 30 of the catheter 1. This can allow a rotational force by the operator to be more efficiently transmitted to the distal end of the catheter 2.

It is noted that there is no particular limitation for a resin material used for forming the outer layer 40a, but polyamide, polyamide elastomer, polyester, polyurethane, and the like may be used as in the outer layer 40.

Next, a catheter 3 according to the disclosed embodiments will be described with reference to FIGS. 9 to 11. Only differences from the catheter 2 shown in FIGS. 5 to 8 will be described. The catheter 3 further includes a braid 90 and an intermediate layer 100 covering the braid 90 between the inner layer 10 and the coil body 30a.

The braid 90 includes a first element wire and a second element wire braided with each other into a network pattern (a mesh pattern). As shown in FIGS. 10 and 11, a total of 6 first element wires and 6 second element wires are braided with each other into a mesh pattern (6×6).

The material(s) of the first element wires and the second element wires of the first braid 90 may be the same or different. For example, the first element wire may be made of tungsten and the second element wire may be made of stainless steel (SUS304). However, there is no particular limitation for the materials, and resin materials (for example, reinforced plastics) may be used other than metal.

There is no particular limitation for a resin material used for forming the intermediate layer 100, but polyamide, polyamide elastomer, polyester, polyurethane, and the like may be used as in the outer layer 40a.

Figure 9:
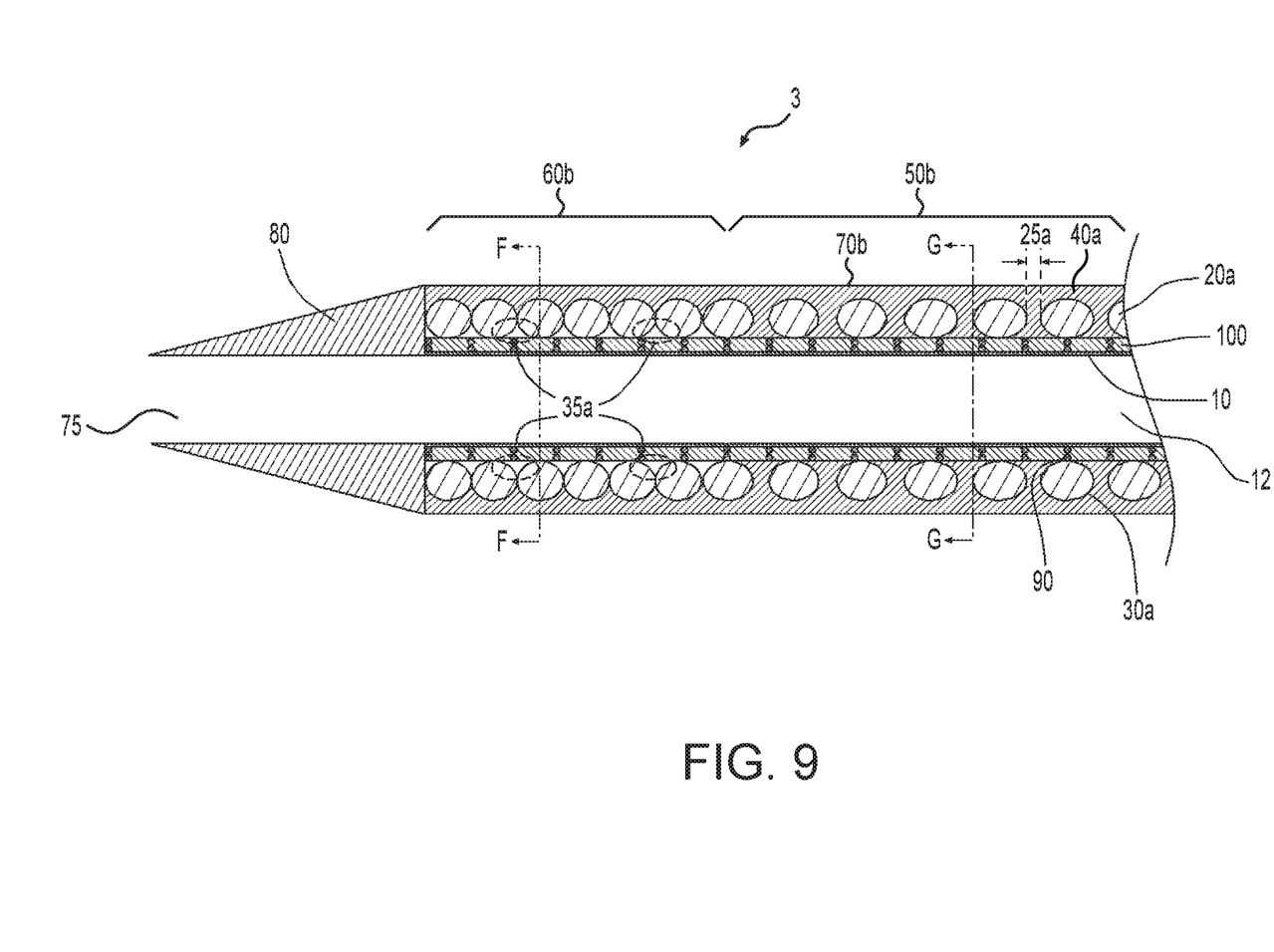
FIG. 9 is a cross-sectional view of a part of a catheter according to the disclosed embodiments.
Figure 10:
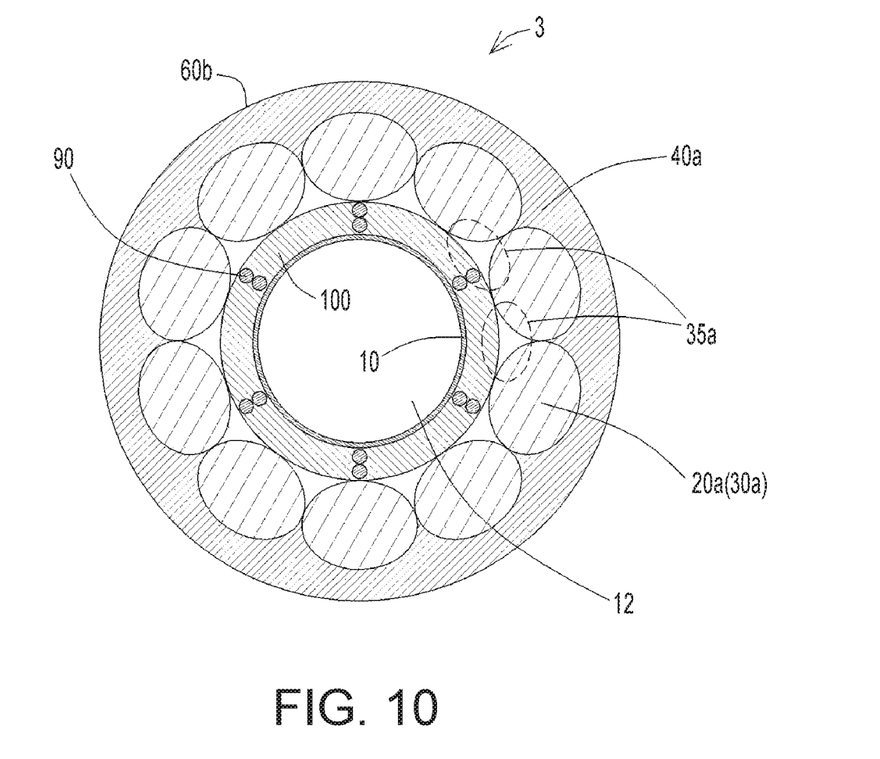
FIG. 10 is a cross-sectional view taken along line F-F of the catheter shown in FIG. 9.
Figure 11:
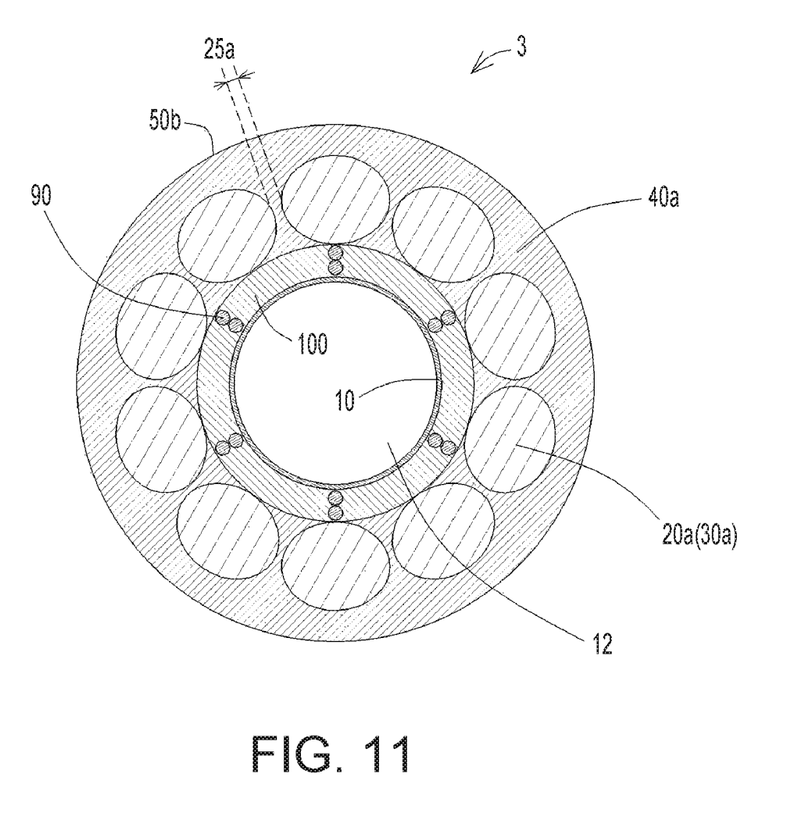
FIG. 11 is a cross-sectional view taken along line G-G of the catheter shown in FIG. 9.

The catheter 3 includes a catheter shaft 70b including a proximal end portion 50b having the gaps 25a between the axially adjacent portions of the element wires 20a where the intermediate layer 100 is directly joined to the outer layer 40a through the gaps 25a between the axially adjacent portions of the element wires 20a; and a distal end portion 60b where the axially adjacent portions of the element wires 20a come into direct contact with each other, and the cavities 35a are formed between the intermediate layer 100 and the coil body 30a, the distal end portion 60b being located at the distal end side relative to the proximal end portion 50b (see FIGS. 9 to 11). In the proximal end portion 50b, the inner layer 10 is joined to the outer layer 40a via the intermediate layer 100 through the gaps 25a.

Specifically as shown in FIGS. 9 and 10, 10 cavities 35a each having a substantially triangular shape in cross section are defined by circumferentially adjacent portions of the element wires 20a and the intermediate layer 100 at the distal end portion 60b of the catheter shaft 70b. Each of the above cavities 35a is formed spirally and axially on the outer periphery of the inner layer 10 along the 10 element wires 20a of the coil body 30a. Further, the adjacent portions of the element wires 20a of the coil body 30a come into contact with each other at the distal end portion 60b of the catheter shaft 70b.

Meanwhile, the outer layer 40a is joined to the intermediate layer 100 through the gaps 25a between the adjacent portions of the element wires 20a at the proximal end portion 50b of the catheter shaft 70b as shown in FIGS. 9 and 11. This means that the element wires 20a of the coil body 30a are covered with and fixed to the intermediate layer 100 and the outer layer 40a along an entire circumference of each of the element wires 20a (and the intermediate layer 100 and the outer layer 40a are directly fixed to each other between the gaps 25a) at the proximal end portion 50b of the catheter shaft 70b.

As described above, the catheter 3 is structured differently between the distal end portion 60b and the proximal end portion 50b. In this configuration, a portion of the circumference of each of the element wires 20a of the coil body 30a is not fixed to either the intermediate layer 100 or the outer layer 40a, and thus the element wires 20a have some degree of freedom and can be flexible enough to be curved at the distal end portion 60b when the catheter 3 is curved. This can improve followability to a pre-inserted curved guide. Further, the adjacent portions of the element wires 20a of the coil body 30a axially coming into contact with each other and having a degree of freedom can allow a rotational force from an operator to be transmitted to the distal end of the catheter 3. Moreover, the element wires 20a of the coil body 30a fixed between the intermediate layer 100 and the outer layer 40a at the proximal end portion 50b can improve the stiffness of the catheter shaft 70b, leading to efficient transmission of a pushing force from an operator.

Further, in the catheter 3, the braid 90 is provided on the outer periphery of the inner layer 10. This can reduce the risk of the lumen 12 becoming crushed, which would prevent sliding of a guide wire, when the element wires 20a of the coil body 30a having a degree of freedom move along the side of the inner layer 10 upon rotation of the catheter 3 in a curved state.

Figure 12:
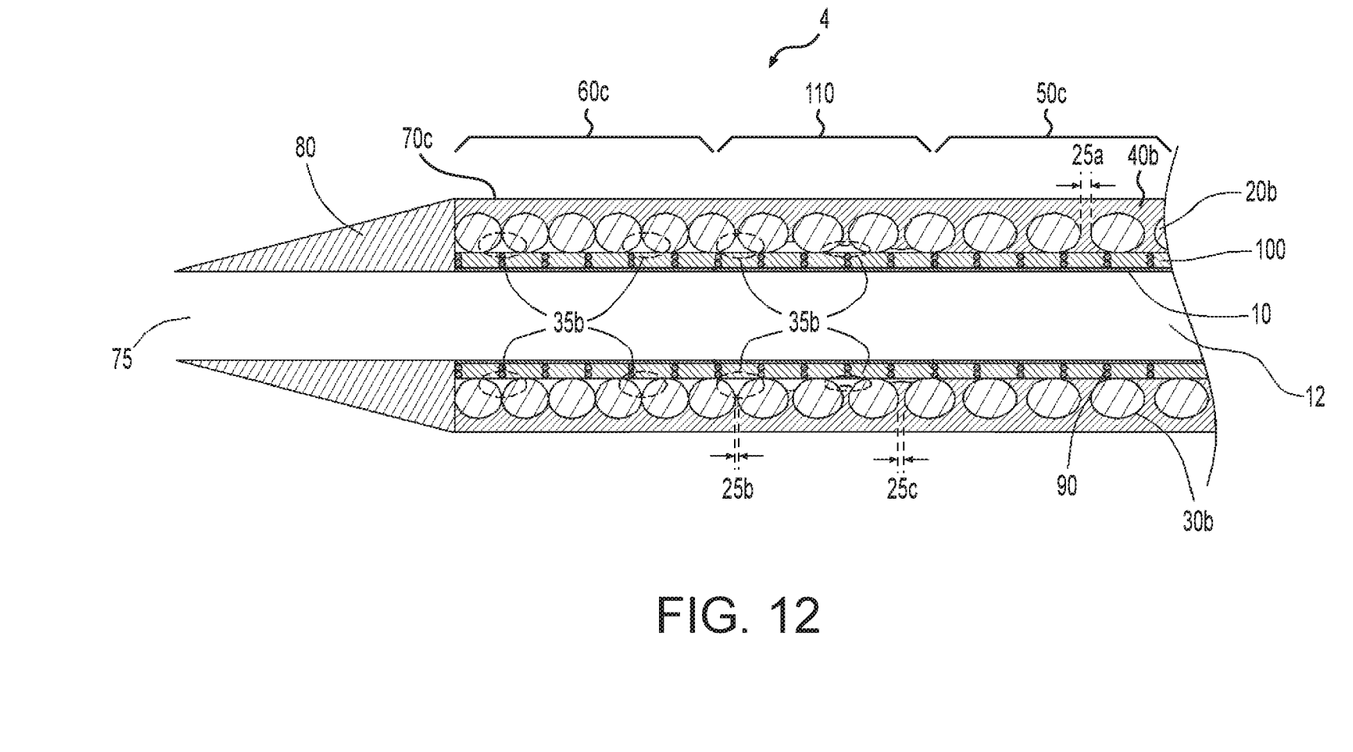
FIG. 12 is a cross-sectional view of a part of a catheter according to the disclosed embodiments.

Next, a catheter 4 according to the disclosed embodiments will be described with reference to FIG. 12. Only differences from the catheter 3 shown in FIGS. 9 to 11 will be described. The catheter 4 additionally includes an intermediate portion 110 where gaps between axially adjacent portions of the element wires 20b become wider from a gap 25b (at a distal end of the intermediate portion 110) to a gap 25c (at a proximal end of the intermediate portion 110), the intermediate portion 110 being located between a proximal end portion 50c and a distal end portion 60c. Cavities 35b of the distal end portion 60c extend to the intermediate layer 110, and the heights (depths in the radial direction) of the cavities 35b gradually decrease toward the proximal end.

Specifically, a catheter shaft 70c of the catheter 4 includes 10 cavities each having a substantially triangular shape in cross section formed between circumferentially adjacent portions of the element wires 20b and the intermediate layer 100 at the distal end portion 60c as in the distal end portion 60b of the catheter shaft 70b of the catheter 3. Each of the above cavities 35b is formed spirally and axially on the outer periphery of the inner layer 10 along the 10 element wires 20b of the coil body 30b. Further, the adjacent portions of the element wires 20b of the coil body 30b come into direct contact with each other at the distal end portion 60c of the catheter shaft 70c.

Meanwhile, at the intermediate portion 110, the heights of the cavities 35b extending from the distal end portion 60c gradually decrease toward the proximal end as the gaps between the axially adjacent portions of the element wires 20b become wider from the gap 25b to the gap 25c. Therefore, the proportion of the circumference of each of the element wires 20b of the coil body 30b covered with and fixed to the outer layer 40b increases toward the proximal end (in other words, the degree of freedom for the element wires 20b decreases toward the proximal end).

In the proximal end portion 50c, the outer layer 40b is directly joined to the intermediate layer 100 through the gaps 25a between the adjacent portions of the element wires 20b as in the proximal end portion 50b of the catheter shaft 70b of the catheter 3. This means that the element wires 20b of the coil body 30b are covered with and fixed to the intermediate layer 100 and the outer layer 40b at the proximal end portion 50c.

As described above, in the catheter 4, the cavities 35b of the distal end portion 60c extend to the intermediate portion 110, and the cavities 35b gradually become smaller toward the proximal end. This configuration can reduce a sudden change in stiffness between the proximal end portion 50c and the distal end portion 60c as compared with the catheter 3, and thus can prevent a kink and/or break between the proximal end portion 50c and the distal end portion 60c.

It is noted that there is no particular limitation for a resin material used for forming the outer layer 40b, but polyamide, polyamide elastomer, polyester, polyurethane, and the like may be used as in the outer layers 40, 40a.

In the above descriptions, the coil body 30 was configured such that the element wire 20 including a single wire is wound spirally in the clockwise direction facing to the distal end side. Further, the coil bodies 30a, 30b were configured such that the element wires 20a, 20b are wound spirally in the clockwise direction facing to the distal end side. However, there is no particular limitation for the winding directions of the element wires 20, 20a, and 20b of the coil bodies 30, 30a, and 30b, respectively, and they may be wound spirally in the counterclockwise direction facing to the distal end side.

Further, in the above descriptions, the cavities 35, 35a, and 35b were each formed spirally and axially on the outer periphery of the inner layer 10 along the element wires 20, 20a, and 20b of the coil bodies 30, 30a, and 30b, respectively. However, the configurations of the cavities 35, 35a, and 35b are not limited to this. For example, flat wires may be used for the element wires 20, 20a, and 20b of the coil bodies 30, 30a, and 30b, respectively, to provide the cavities 35, 35a, and 35b each with a tubular shape in cross section between the inner layer 10 and the coil bodies 30, 30a, and 30b, respectively.

Moreover, in the catheters 2 to 4, 10 cavities 35a having a substantially triangular shape defined by the circumferentially adjacent portions of the element wires 20a and the inner layer 10, or the 10 cavities 35a, 35b each having a substantially triangular shape defined by the circumferentially adjacent portions of the element wires 20a and the intermediate layer 100, were provided at the distal end portions 60a, 60b, 60c, respectively. This means that the number of the cavities 35a, 35b was in agreement with the number of the element wires 20a, 20b of the coil bodies 30a, 30b, respectively. However, there is no particular limitation for the number of the cavities 35a, 35b. For example, three of the cavities 35a, 35b may be filled with resin layers, and the remaining 7 cavities may remain empty spaces and be used as the cavities 35a, 35b.

It is noted that the catheter 4 was described based on the catheter 3. However, it is not limited to this. The description may also be based on the catheters 1 and 2. Specifically, in the catheters 1, 2, the intermediate portion 110 where the gaps 35, 35a between the axially adjacent portions of the element wires 20, 20a become wider toward the proximal end may be provided between the proximal end portions 50, 50a and the distal end portions 60, 60a, and the cavities 35, 35a of the distal end portions 60, 60a may extend to the intermediate portion 110, and the heights of the cavities 35, 35a may gradually decrease toward the proximal end (not shown).

Proximal

What is claimed is:
1. A catheter comprising:
   an inner layer;
   a coil body including one or more element wires wound around an outer periphery of the inner layer; and
   an outer layer covering an outer periphery of the coil body,
wherein:
   gaps are provided between axially adjacent portions of the one or more element wires in at least a proximal end portion of the catheter, and the outer layer extends through the gaps in the proximal end portion to contact the inner layer; and
   in at least a distal end portion of the catheter,
      the coil body covers the entire outer periphery of the inner layer at a distalmost end of the inner layer,
      the axially adjacent portions of the one or more element wires come into contact with each other, and
      one or more cavities are formed between the inner layer and the coil body.

2. The catheter according to claim 1, wherein the contact between the inner layer and the outer layer in the proximal end portion is direct contact.

3. The catheter according to claim 1, wherein the one or more cavities are spirally formed on the outer periphery of the inner layer in an axial direction of the catheter along the one or more element wires.

4. The catheter according to claim 1, wherein:
   the coil body includes a plurality of the element wires wound around an outer periphery of the inner layer, and in at least the distal end portion, a plurality of the cavities are formed between the inner layer and the coil body.

5. The catheter according to claim 1, wherein in at least the distal end portion, the one or more element wires are movable with respect to the inner layer.

6. The catheter according to claim 1, wherein the proximal end portion is stiffer than the distal end portion.

7. The catheter according to claim 1, wherein:
the inner layer, the coil body, and the outer layer form a shaft,
the catheter further comprises a distal tip joined to a distal end of the shaft, and
a distal end of the one or more element wires comes into direct contact with the distal tip, forming a cavity between the inner layer and the coil body.

8. The catheter according to claim 1, wherein:
the gaps are further provided in an intermediate portion of the catheter that extends from a distal end of the proximal end portion to a proximal end of the distal end portion, and
the outer layer contacts the inner layer only in the intermediate portion and the proximal end portion.

9. A catheter comprising:
an inner layer;
a coil body including one or more element wires wound around an outer periphery of the inner layer; and
an outer layer covering an outer periphery of the coil body,
wherein:
gaps are provided between axially adjacent portions of the one or more element wires in at least a proximal end portion of the catheter, and the outer layer extends through the gaps in the proximal end portion to contact the inner layer; and
in at least a distal end portion of the catheter,
the axially adjacent portions of the one or more element wires come into contact with each other, and
one or more cavities are formed between the inner layer and the coil body,
the gaps are further provided in an intermediate portion of the catheter located between the proximal end portion and the distal end portion, and become wider from a distal end of the intermediate portion toward a proximal end of the intermediate portion; and
the one or more cavities extend from the distal end portion into the intermediate portion, and the height of the one or more cavities gradually decreases toward the proximal end of the intermediate portion.

10. The catheter according to claim 9, wherein the contact between the inner layer and the outer layer in the proximal end portion is direct contact.

11. The catheter according to claim 9, wherein the one or more cavities are spirally formed on the outer periphery of the inner layer in an axial direction of the catheter along the one or more element wires.

12. The catheter according to claim 9, wherein:
the coil body includes a plurality of the element wires wound around an outer periphery of the inner layer, and
in at least the distal end portion, a plurality of the cavities are formed between the inner layer and the coil body.

13. The catheter according to claim 9, wherein in at least the distal end portion, the one or more element wires are movable with respect to the inner layer.

14. The catheter according to claim 9, wherein the proximal end portion is stiffer than the distal end portion.

* * * * *